(12) United States Patent
Castellin et al.

(10) Patent No.: US 8,207,339 B2
(45) Date of Patent: Jun. 26, 2012

(54) PROCESS FOR PREPARING MOXIFLOXACIN AND SALTS THEREOF

(75) Inventors: Andrea Castellin, Mestrino (IT); Pierluigi Padovan, Casale sul Sile (IT); Liu Jiageng, Hangzhou (CN); Yibo Zhou, Hangzhou (CN); Lin Feng, Hangzhou (CN)

(73) Assignee: F.I.S. Fabbrica Italiana Sintetici S.p.A., Alte di Montechhio Maggiore, Vicenza (IT)

( * ) Notice: Subject to any disclaimer, the term of this patent is extended or adjusted under 35 U.S.C. 154(b) by 0 days.

(21) Appl. No.: 13/051,081

(22) Filed: Mar. 18, 2011

(65) Prior Publication Data

US 2011/0230661 A1      Sep. 22, 2011

(30) Foreign Application Priority Data

Mar. 19, 2010 (IT) .......................... MI2010A000450

(51) Int. Cl.
*C07D 471/04* (2006.01)
(52) U.S. Cl. ....................................................... 546/113
(58) Field of Classification Search ........................ None
See application file for complete search history.

(56) References Cited

U.S. PATENT DOCUMENTS

2006/0264635 A1* 11/2006 Satyanarayana et al. ..... 546/113

FOREIGN PATENT DOCUMENTS

| DE | 197 51 948 A1 | 5/1999 |
|---|---|---|
| EP | 0 550 903 A1 | 7/1993 |
| EP | 0 657 448 A1 | 6/1995 |

OTHER PUBLICATIONS

Iztok Turel, The Interactions of Metal Ions with Quinolone Antibacterial Agents, 232 Coordination Chem. Rev. 27-47 (2002).*
Chen et al., X-Ray Crystal Structures of Mg2+ and Ca2+ Dimers of the Antibacterial Drug Norfloxacin, J. Chem. Soc. Dalton Trans. 4013-14 (2000).*

* cited by examiner

*Primary Examiner* — Janet Andres
*Assistant Examiner* — Timothy R Rozof
(74) *Attorney, Agent, or Firm* — Dickstein Shapiro LLP

(57) ABSTRACT

The present invention relates to a process for the synthesis of Moxifloxacin of Formula (I) and salts thereof (I)

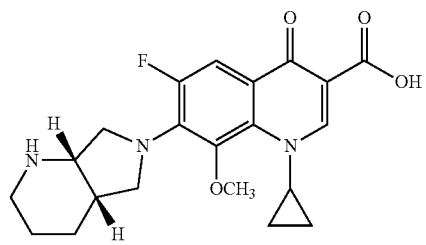

by means of a process providing the coupling reaction of 1-cyclopropril-6,7-difluoro-1,4-dihydro-8-methoxy-4-oxo-3-quinolinic acid or ester thereof with (4aS, 7aS)-octahydro-1H-pyrrole[3,4-b]pyridine using a magnesium salt.

19 Claims, No Drawings

PROCESS FOR PREPARING MOXIFLOXACIN AND SALTS THEREOF

FIELD OF THE INVENTION

The object of the present invention is a process for preparing Moxifloxacin and salts thereof.

BACKGROUND ART

Moxifloxacin is a broad-spectrum fluoroquinolone antibacterial agent, used for treating respiratory infections (pneumonia, chronic sinusitis, chronic bronchitis) sold in the hydrochloride form from Bayer AG under the name of Avelox® and Avalox®. It is also sold by Alcon Inc. in a low-dosage form for ophthalmic use under the name of Vigamox®.

Moxifloxacin of Formula I and having the chemical name of 1-cyclopropyl-7-[(1S,6S)-2,8-diazabicyclo [4.3.0]non-8-yl]-6-fluoro-8-methoxy-4-oxo-quinoline-3-carboxylic acid, is characterized by a fluoroquinolone structure, similar to that of other two antibiotics of the same class (Gatifloxacin and Balofloxacin), and a side chain consisting of (4aS,7aS)-octahydro-1H -pyrrole[3,4-b]pyridine.

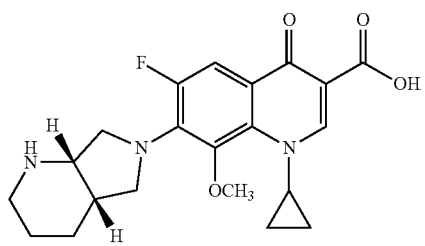

(I)

The fluoroquinolone intermediate of Formula (II), with the 8-methoxy group and the one with the 8-fluorine group of Formula (VIII) are both commercially available products.

The (4aS, 7aS)-octahydro-1H-pyrrole[3,4-b]pyridine, also called the (S,S)-2,8-diazabicyclo[4.3.0]nonane and having CAS RN [151213-40-0] of Formula (III), is the Moxifloxacin side chain and is the synthesis key intermediate as it has two chiral centers, both with S configuration, is optically active and levogyrous. The preparation of the same is also described in the two Italian patent applications MI2009A001353 and MI2009A000332 both issued to FIS Fabbrica Italiana Sintetici Spa which provide an optimized optical resolution process and a regio and stereo-selective synthesis process of bio-enzymatic type respectively.

A first prior art synthesis process of Moxifloxacin hydrochloride described in EP 550903 comprises the coupling reaction between 1-cyclopropril -6,7-difluoro-1,4-dihydro-8-methoxy-4-oxo-3-quinolinic acid of Formula II

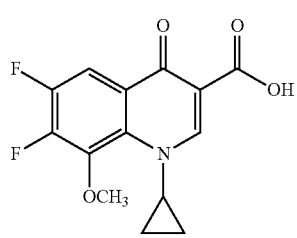

(II)

with the intermediate (4aS, 7aS)-octahydro-1H -pyrrole[3,4-b]pyridine of Formula III in the presence of base:

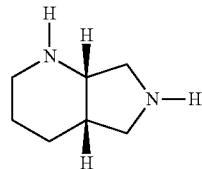

(III)

Due to the low regioselectivity of the reaction, however, the product obtained contains the isomer 6 impurity of Formula (V)

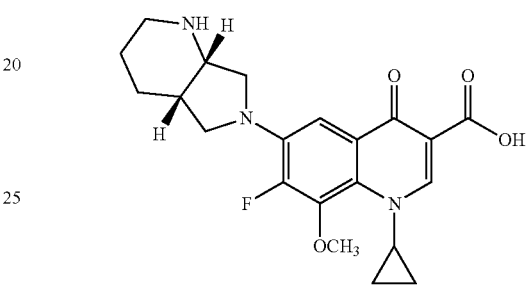

as the major impurity, which is difficult to separate from the product as this is a position isomer.

The required chromatographic purification on silica gel column results in the obtainment of the same in low yields.

WO 2008/138759 describes a process for preparing Moxifloxacin hydrochloride monohydrate where the coupling reaction between 1-cyclopropril-6,7-difluoro -1,4-dihydro-8-methoxy-4-oxo-3-quinolinic acid with (S,S)-2,8-diazabicyclo[4.3.0]nonane is carried out in the absence of a base and the Moxifloxacin is isolated as the L-Tartrate or Fumarate or p-Ditoluiltartrate to be purified from the isomer 6 impurity, then it is converted to Moxifloxacin hydrochloride.

A second prior art method for the synthesis of Moxifloxacin described in WO 2005/012285 comprises the reaction between 1-cyclopropyl-6,7-difluoro-1,4-dihydro -8-methoxy-4-oxo-3-quinolinic acid ethyl ester of Formula (VII)

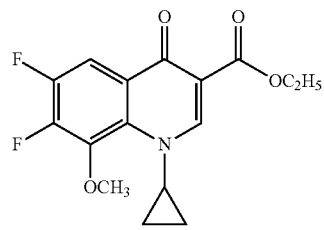

(VII)

with boric acid and acetic anhydride to form an intermediate borate complex with 95% yield, which is reacted with (4aS, 7aS)-octahydro-1H-pyrrole[3,4-b]pyridine of Formula (III) with 72% yield, the ester and complex being subsequently hydrolyzed, and then salified to give Moxifloxacin hydrochloride with 91% yield, with 62% total molar yield.

In WO 2008/059223, a similar process is used as above, wherein, however, the complex is generated using boric acide and proprionic anhydride in place of acetic anhydride.

A third method reported in WO 2006/134491 provides reacting 1-cyclopropril-6,7-difluoro-1,4-dihydro-8-methoxy-4-oxo-3-quinolinic acid of Formula (II) with boron trifluoride etherate to give a difluoroborate intermediate which is reacted with (S,S) -2,8-diazabicyclo[4.3.0]nonane of Formula (III) in the presence of a base with 92% yield thereby obtaining a Moxifloxacin difluoroborate complex which is hydrolyzed and salified to give Moxifloxacin hydrochloride with 42 to 55% total yield.

Finally, the Moxifloxacin synthesis has been carried out, as discussed in EP 1832587, by means of a similar method as above, the latter being carried out one-pot and including silanization prior to complexation by means of boron trifluoride.

The methods described above result in unsatisfying yields and suffer from using toxic reactants such as boron trifluoride.

SUMMARY OF THE INVENTION

The issue addressed by the present invention is thus to provide a different effective process for preparing Moxifloxacin using a more regioselective reaction avoiding the isomer-6 impurity, results in high yields and avoids using toxic reactants as $BF_3$, thereby allowing to at least partially overcoming the drawbacks cited herein above with reference to prior art.

This problem is solved by means of a method for the synthesis of Moxifloxacin as stated in the annexed claims, the definitions of which being part of the present disclosure.

Further characteristics and advantages of the process according to the invention will result from the description herein below of preferred exemplary embodiments, which are given as indicative and non-limiting examples.

DETAILED DESCRIPTION OF THE INVENTION

According to a general aspect, the present invention relates to a method for the synthesis of Moxifloxacin or ester thereof of Formula (X) or salt thereof:

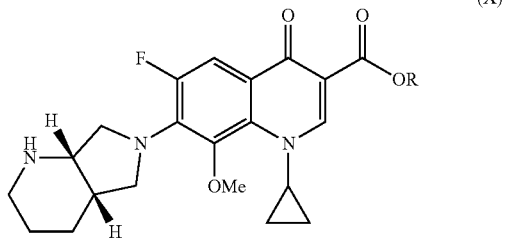

wherein R is an optionally substituted hydrogen or linear or branched C1-C4 alkyl or an optionally substituted phenyl or benzyl, comprising the coupling reaction of 1-cyclopropyl -6,7-difluoro-1,4-dihydro-8-methoxy-4-oxo-3-quinolinic acid or ester thereof of Formula (XI):

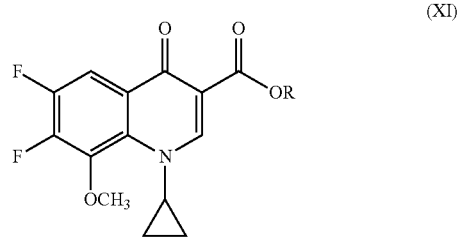

wherein R is optionally substituted hydrogen or linear or branched C1-C4 alkyl or an optionally substituted phenyl or benzyl, with (4aS, 7aS)-octahydro-1H-pyrrole[3,4-b]pyridine of Formula (III):

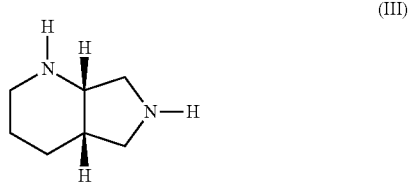

carried out in the presence of a magnesium salt.

R is preferably selected from hydrogen, methyl and ethyl.

Particularly, the present invention relates to a process for the synthesis of Moxifloxacin of Formula (I) and salts thereof:

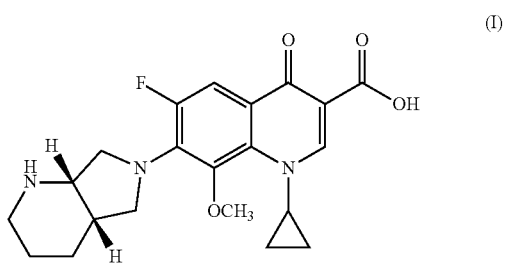

by means of the following method which provides the coupling reaction of 1-cyclopropril-6,7-difluoro-1,4-dihydro-8-methoxy-4-oxo-3-quinolinic acid of Formula (II):

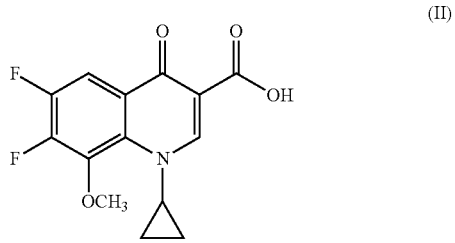

with (4aS, 7aS)-octahydro-1H-pyrrole[3,4-b]pyridine of Formula (III):

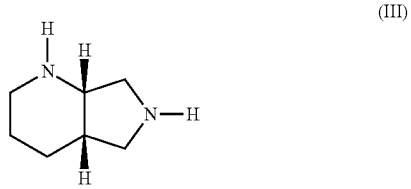

using a magnesium salt, optionally in the presence of a base.

It has been surprisingly found that using a magnesium salt or a magnesium salt in the presence of a base allows considerably improving the regioselectivity of the coupling reaction described above, thereby allowing obtaining purer Moxifloxacin in higher yields because the formation of isomer 6 impurity is avoided, using non-toxic reactants.

The presence of magnesium is likely to result in the formation of intermediate complexes with 1:1 stechiometry with the fluoroquinolone intermediate as illustrated in Scheme (I)

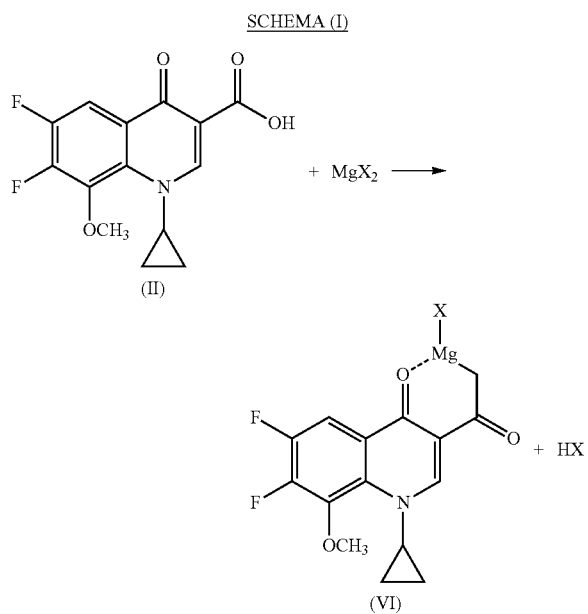

which facilitate the nucleophilic substitution of fluoride in position 7 by the (4aS, 7aS)-octahydro-1H -pyrrole[3,4-b]pyridine rather than the substitution of the fluoride in position 6, thereby preventing the formation of the isomer 6 impurity. Scientific evidences relative to the existence of magnesium complexes with kinolin-carboxylic acids with magnesium having 1:1 stechiometry are described in the Journal of Molecular Structure (2004), 691(1-3), 107-113, which reports crystallographic data of the complexes with ofloxacin and in U.S. Pat. No. 5,334,589 which describes the use of the complexes, particularly of Temafloxacin, for pharmaceutical formulations.

The reaction can be first carried out by forming the complex of 1-cyclopropyl-6,7-difluoro-1,4-dihydro-8-methoxy-4-oxo-3-quinolinic acid with magnesium and thereafter adding the (4aS, 7aS)-octahydro-1H -pyrrole[3,4-b]pyridine.

In an embodiment, the addition of the magnesium salt to the 1-cyclopropyl-6,7-difluoro-1,4-dihydro-8-methoxy-4-oxo-3-quinolinic acid in order to form the complex thereof can be also carried out in the presence of the other (4aS, 7aS)-octahydro-1H-pyrrole[3,4-b]pyridine intermediate.

The magnesium salts that can be used are, by way of non-limiting examples, magnesium hydroxide, carbonate, bicarbonate, sulfate, chloride, bromide, iodide, etc., C1-C4 alkoxy, or having an organic acid such as acetate, oxalate, citrate, methane sulfonate, etc. as the counter-ion thereof. Mixtures of magnesium salts can be also used. Among the preferred salts for use in the reaction are magnesium hydroxide and magnesium carbonate, bicarbonate, sulfate and methoxy.

The molar equivalents of magnesium salt to be used can suitably be higher than one relative to the 1-cyclopropyl-6,7-difluoro-1,4-dihydro-8-methoxy-4-oxo-3-quinolinic acid and range between 1 and 5. In a preferred embodiment of the invention the molar equivalents of magnesium salt to be used range between 1 and 3 and more preferably about 1.5.

In an embodiment, in order to displace the equilibrium and thereby facilitate the formation of the magnesium complex, a base (also a weak one), either organic or inorganic, can be optionally used.

The organic bases that can be used are for example DBU, DIPEA, DABCO, TEA, N-Methylmorpholine.

The formation of the magnesium complex of Formula VI can be also facilitated by optionally distilling any alcohol that may be generated when a magnesium C1-C4 alkoxy salt is used, such as methylated or ethylated magnesium.

In an embodiment, the solvent in which the reaction can be carried out can be suitably selected from NMP, DMSO, ACN, DMF, DMAc; preferred solvents in which the reaction can be carried out are NMP and DMSO.

In an embodiment of the invention, the reaction can be carried out using 1 to 50 volumes of solvent relative to the 1-cyclopropyl-6,7-difluoro-1,4-dihydro -8-methoxy-4-oxo-3-quinolinic acid substrate, most suitably 1 to 10 volumes of solvent, preferably about 5 volumes can be used.

The temperature for carrying out the reaction can range between 20° C. and 100° C., more preferably between 50° C. and 90° C.

The molar equivalents of (4aS, 7aS)-octahydro-1H -pyrrole[3,4-b]pyridine to be used range between 1.0 and 3.0 relative to the 1-cyclopropyl-6,7-difluoro-1,4-dihydro-8-methoxy-4-oxo-3-quinolinic acid substrate, more preferably the molar equivalents range between 1.2 and 1.5.

The addition of (4aS, 7aS)-octahydro-1H -pyrrole[3,4-b] pyridine of Formula (III) to the solution containing the magnesium complex can be suitably carried out by dissolving it in the same solvent used for the reaction and by dosing it in the reaction mixture over a time ranging between 10 and 60 minutes.

In an embodiment, a phase transferring agent can be used for carrying out the reaction. Merely by way of example, Tetrabutylammonium chloride, bromide or iodide can be used. The amount of phase transferring agent to be used can suitably range between 0.1% and 10% by weight relative to the 1-cyclopropril-6,7-difluoro-1,4-dihydro-8-methoxy-4-oxo-3-quinolinic acid substrate.

In a variant embodiment of the Moxifloxacin synthesis method described above, the coupling reaction mediated by magnesium salts provides the following steps:

(A) condensation of the (4aS, 7aS)-octahydro-1H -pyrrole[3, 4-b]pyridine intermediate of Formula (III) with a fluoroquinolone of Formula (VIII):

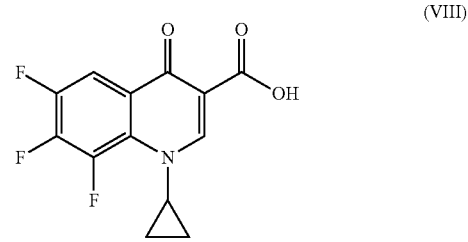

to give the intermediate of Formula (IX):

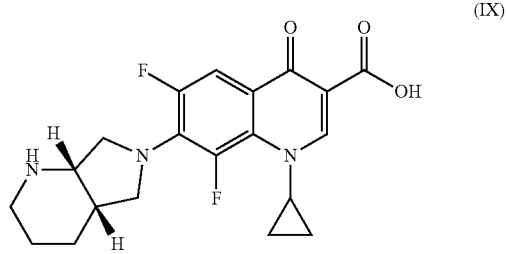

(B) methoxylation of the intermediate (IX) to give free base Moxifloxacin (I);

(C) optionally, salification with hydrogen chloride to give Moxifloxacin hydrochloride.

The fluoroquinolone intermediate of Formula (VIII), reacts with the intermediate of Formula (III) using a magnesium salt with the same behavior of the fluoroquinolone intermediate of Formula (II).

The methoxylation reaction, according to step B, can be carried out according to the teachings known to those skilled in the art, such as those described in patents EP 0 350 733 A1, EP 0 757 990 A1, EP 0 550 903 A1, EP 1 034 173 A1, WO 2006/052264, WO 2005/012285, WO 2006/134491 and EP 1 832 587 A1.

In an embodiment, the thus-obtained Moxifloxacin can be optionally converted into a salt thereof by means of dissolution within a suitable organic solvent and addition of the acid thereof.

Particularly, Moxifloxacin can be converted into Moxifloxacin hydrochloride, according to step C, by means of treatment with hydrochloric acid within a suitable organic solvent or water.

EXPERIMENTAL PART

Example 1

Synthesis of Moxifloxacin HCl
(I-HCl)—Exemplifying the Invention

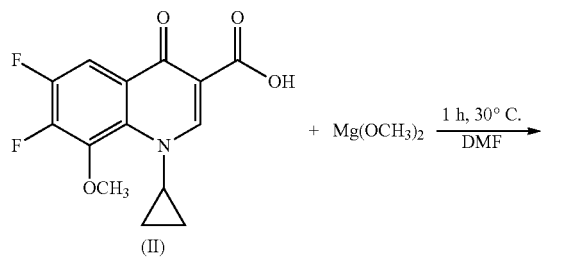

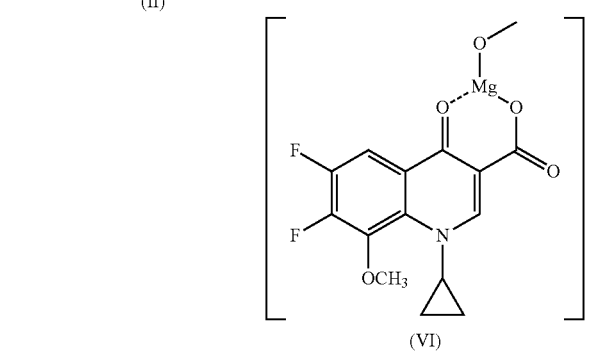

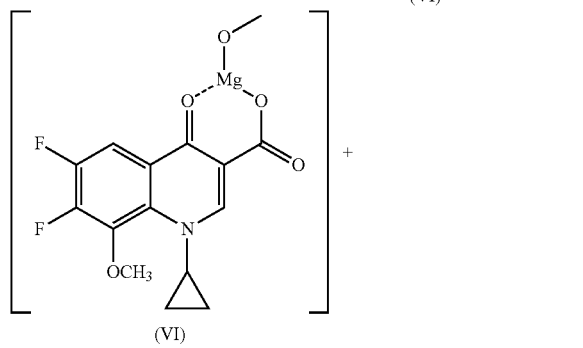

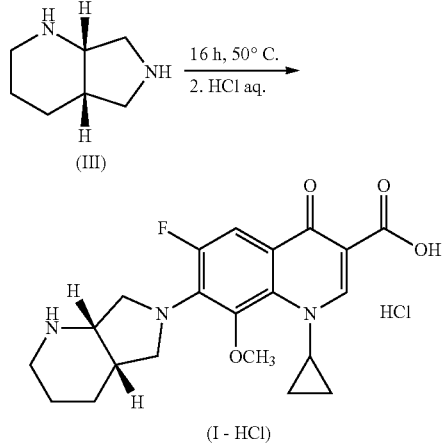

In a 250 mL three-neck flask provided with a mechanical stirrer, thermometer and thermostat, 20.0 g of 1-cyclopropyl-6,7-difluoro-1,4-dihydro-8-methoxy-4-oxo-3-quinolinic acid (67.74 mmol), 7.37 g of magnesium methoxide (85.3 mmol, 1.26 mol. eq.), 4.33 g of magnesium hydroxide (74.2 mmol, 1.10 mol. eq.) and 120 mL of dimethylformamide (DMF) (6 vol.) were loaded under inert atmosphere.

The mixture is heated at 30° C. for one hour and the methanol which is formed is removed by means of low pressure distillation. To the solution is then added 0.5 g of tetrabutylammonium chloride (TBAC) (2.5% by weight on the substrate. 10.25 g of (4aS, 7aS)-Octahydro-1H-pyrrole[3,4-b]pyridine (81.29 mmol, 1.20 mole equiv.) is then added.

The reaction mixture is heated at 45° C. and maintained at T=45-50° C. until the HPLC monitored reaction is completed, i.e. about 16 hours.

The solvent is vacuum distilled and about 110 mL DMF are recovered. To the residual suspension 200 mL water and 25 mL HCl 12 N (300 mmol) is added, thereby bringing the solution pH to 3-4. The suspension is heated at 30° C. and stirred at that temperature for 30 minutes, then it is cooled at T<10° C. and, after the product has precipitated, it is stirred at this temperature for 30 minutes. The suspension is filtered and the solid is washed with water. The crude is dissolved in 150 mL hydrochloric acid 5.5 mol/L. The whole is stirred for at least 20 minutes until it is dissolved. The small amount of insolute material, being an impurity, is eliminated through filtration. The filtrate is concentrated to a small volume under low pressure. To the obtained solution is added 70 mL anhydrous ethanol. The mixture is stirred and cooled below 5° C. for at least one hour after solid precipitation. The suspension is filtered and the solid is washed with mL ethyl acetate. The solid is vacuum dried for 3 hours at 25° C. then at Tmax.=70° C. for 4 hours. 26.4 g of Moxifloxacin hydrochloride is obtained (molar yield=89%) with HPLC (A %) purity>99.0%.

Example 2

Synthesis of Moxifloxacin HCl (I-HCl)

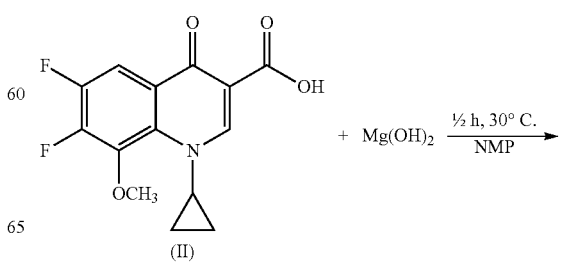

Example 3

Synthesis of Moxifloxacin HCl (I-HCl)

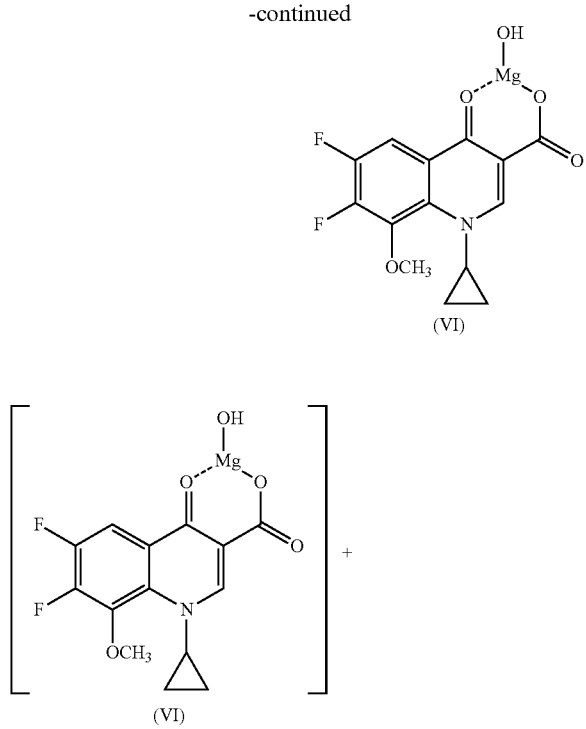

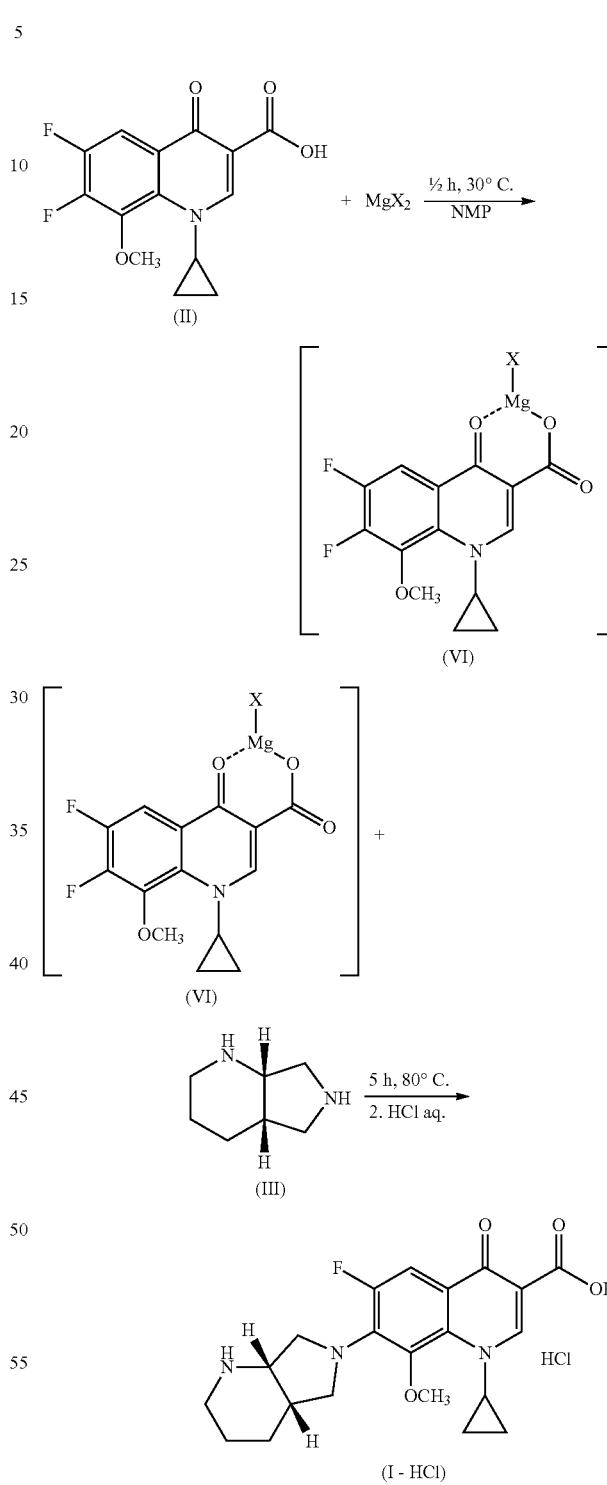

In a 250 mL three-neck flask provided with a mechanical stirrer, thermometer and thermostat 20.0 g of the 1-cyclopropyl-6,7-difluoro-1,4-dihydro-8-methoxy-4-oxo-3-quinolinic acid (67.74 mmol), 5.9 g of Magnesium hydroxide (101.2 mmol, 1.50 mol. eq.) and 80 mL of N-methyl pyrrolidone (NMP) (4 vol.) were loaded under inert atmosphere.

The mixture is heated at 30° C. for half an hour. To the solution is then added 12.8 g of (4aS, 7aS)-octahydro-1H-pyrrole[3,4-b]pyridine (101.5 mmol, 1.50 molar equiv.).

The reaction mixture is heated at 80° C. and maintained at this temperature until the HPLC-monitored reaction is completed, i.e. for about 5 hours.

99.95% conversion, 88.0% Moxifloxacin (HPLC A %).

The reaction is quenched by means of the addition of 300 mL of diluted hydrochloric acid.

The experiment described in the Example 2 has been repeated under the same conditions, however, the type of magnesium salt used has been changed and 1.50 molar equivalents have been used as above. The following table shows the results obtained at the reaction control level which has been sampled after 5 hours.

| Mg salt | % Conversion (HPLC) | HPLC Moxifloxacin (A %) |
|---|---|---|
| Mg(OH)2 (Example 2) | 99.95 | 88.0 |
| MgSO4 | 99.79 | 88.5 |
| MgCO3 | 99.88 | 88.4 |

Example 4

Synthesis of 1-cyclopropyl-6,8-difluoro-1,4-dihydro-7-[(4aS,7aS)-octahydro-6H-pyrrole[3,4-b]piridin-6-il]-4-oxo-3-quinolincarbossilic acid, of Formula (IX), intermediate of Moxifloxacin

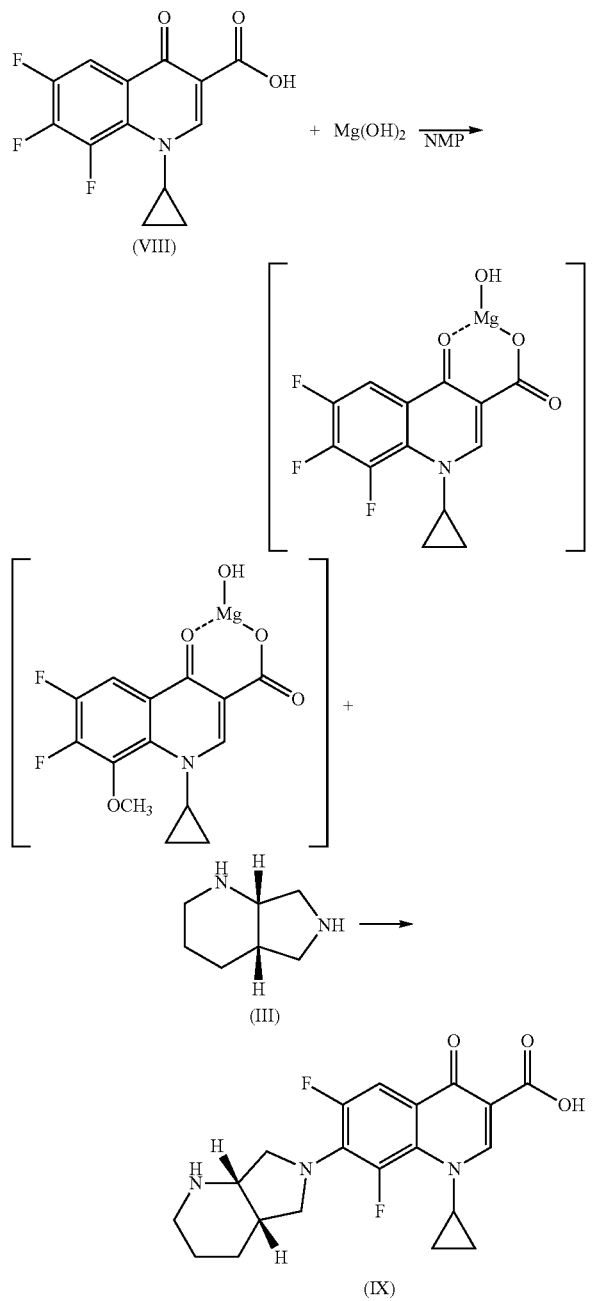

In a 250 mL three-neck flask provided with mechanical stirrer, 19.2 g of 1-cyclopropyl-6,7,8-trifluoro-1,4-dihydro-4-oxo-3-quinolinic acid (67.80 mmol), 5.9 g of magnesium hydroxide (101.2 mmol, 1.50 mol. eq.) and 80 mL of N-methylpyrrolidone (NMP) (4 vol.) were loaded under inert atmosphere.

The mixture is heated at 30° C. for half an hour. To the solution is then added 12.8 g of (4aS, 7aS)-octahydro-1H-pyrrole[3,4-b]pyridine (101.5 mmol, 1.50 molar equiv.).

The reaction mixture is heated at 80° C. and maintained at that temperature until the HPLC monitored reaction is completed, i.e. for about 5 hours. 99.82% conversion, 87.86% Moxifloxacin (HPLC A%). The reaction is quenched by means of the addition of 300 mL of diluted hydrochloric acid.

In view of what has been described above, those skilled in the art will be able to appreciate the advantages provided by the process of the present invention.

Particularly, it will be appreciated how Moxifloxacin can be obtained in pure form with good yields using the conditions being the object of the present invention allows, thus reducing the process operability and yield loss, while using toxic reagents.

The invention claimed is:

1. A method for the synthesis of Moxifloxacin or ester thereof of Formula (X) or salt thereof:

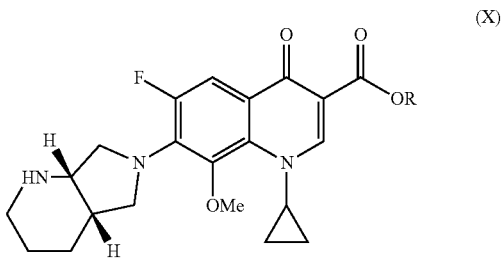

wherein R is an optionally substituted hydrogen or linear or branched C1-C4 alkyl or an optionally substituted phenyl or benzyl, comprising coupling a 1-cyclopropyl-6,7-difluoro-1,4-dihydro-8-methoxy-4-oxo-3-quinolinic acid or ester thereof of Formula (XI):

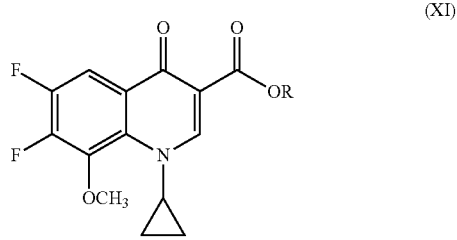

wherein R is an optionally substituted hydrogen or linear or branched C1-C4 alkyl or an optionally substituted phenyl or benzyl, with a (4aS, 7aS)-octahydro-1H-pyrrole[3,4-b]pyridine of Formula (III):

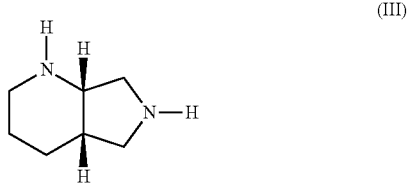

in the presence of a magnesium salt.

2. The method according to claim 1 wherein R is hydrogen or linear or branched C1-C4 alkyl.

3. The method according to claim 2 wherein R is hydrogen.

4. The method according to claim 2 wherein R is methyl or ethyl.

5. The method according to claim 1, comprising converting the Moxifloxacin ester into Moxifloxacin free base or a salt thereof.

6. The method according to claim 1, further comprising converting the Moxifloxacin free base into Moxifloxacin hydrochloride.

7. The method according to claim 1, wherein the magnesium salt comprises at least one of a magnesium salt with an organic counter ion and a magnesium salt with an inorganic counter ion.

8. The method according to claim 7 wherein the counter ion is at least one of hydroxide, carbonate, bicarbonate, sulfate, chloride, bromide, iodide, and C1-C4 alkoxy.

9. The method according to claim 7 wherein the magnesium salt is magnesium hydroxide, methylated magnesium, or magnesium carbonate.

10. The method according to claim 7 wherein the organic counter ion is at least one of acetate, oxalate, citrate, and methane sulfonate.

11. The method according to claim 1 further comprising adding the magnesium salt to a mixture of the 1-cyclopropyl-6,7-difluoro-1,4-dihydro-8-methoxy-4-oxo-3-quinolinic acid or ester thereof of Formula (XI) and the (4aS, 7aS)-octahydro-1H-pyrrole[3,4-b]pyridine intermediate of Formula (III).

12. The method according to claim 1, wherein the magnesium salt is present in a range of 1 to 10 molar equivalents relative to the 1-cyclopropyl-6,7-difluoro-1,4-dihydro-8-methoxy-4-oxo-3-quinolinic acid or ester thereof of Formula (XI).

13. The process according to claim 12 wherein the magnesium salt is present in a range of 1 to 2 molar equivalents relative to the 1-cyclopropyl-6,7-difluoro-1,4-dihydro-8-methoxy-4-oxo-3-quinolinic acid or ester thereof of Formula (XI).

14. The method according to claim 1, further comprising adding at least one base to the coupling reaction.

15. The method according to claim 14 wherein the base comprises at least one of DBU, DIPEA, DABCO, TEA, and N-Methylmorpholine.

16. The method according to claim 1 wherein the coupling reaction is carried out in a solvent comprising at least one of NMP, DMSO, ACN, DMF, and DMAc.

17. The method according to claim 1 wherein the reaction is carried out using 1 to 50 volumes of solvent relative to the volume of 1-cyclopropyl-6,7-difluoro-1,4-dihydro-8-methoxy-4-oxo-3-quinolinic acid substrate or ester thereof of Formula (XI).

18. The method according to claim 1 wherein the (4aS, 7aS)-octahydro-1H-pyrrole[3,4-b]pyridine of Formula (III) is present in a range of 1.0 molar equivalents to 3.0 molar equivalents relative to the 1 cyclopropyl-6,7-difluoro -1,4-dihydro-8-methoxy-4-oxo-3-quinolinic acid substrate or ester thereof of Formula (XI).

19. A method for the synthesis of Moxifloxacin or salts thereof of Formula (I) comprising the following steps:

(A) condensation of the (4aS, 7aS)-octahydro-1H-pyrrole [3,4-b]pyridine intermediate of Formula (III), carried out in the presence of a magnesium salt, with a fluoroquinolone of Formula (VIII):

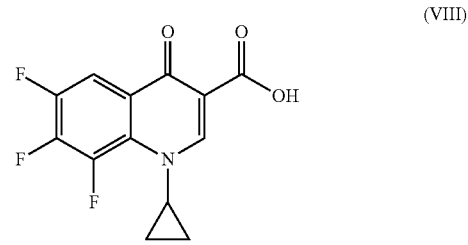

to give the intermediate of Formula (IX):

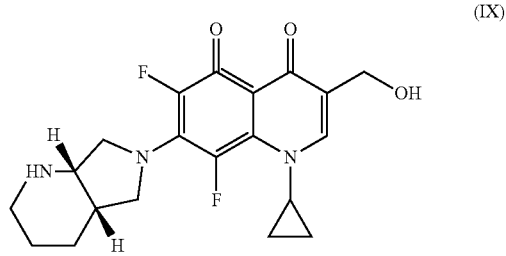

(B) methoxylation of the intermediate (IX) to give free base Moxifloxacin (I);

(C) optionally, salification with hydrogen chloride to give Moxifloxacin hydrochloride.

* * * * *